(12) United States Patent
Zupancic (10) Patent No.: US 9,284,320 B2
(45) Date of Patent: Mar. 15, 2016

(54) TICAGRELOR ADDUCTS WITH DIVALENT METAL SALTS (71) Applicant: Lek Pharmaceuticals d.d., Ljubljana (SI)

(72) Inventor: Borut Zupancic, Ljubljana (SI)

(73) Assignee: Lek Pharmaceuticals d.d. (SL)

( * ) Notice: Subject to any disclaimer, the term of this patent is extended or adjusted under 35 U.S.C. 154(b) by 0 days.

(21) Appl. No.: 14/411,553

(22) PCT Filed: Jul. 3, 2013

(86) PCT No.: PCT/EP2013/064031
§ 371 (c)(1),
(2) Date: Dec. 29, 2014

(87) PCT Pub. No.: WO2014/006091
PCT Pub. Date: Jan. 9, 2014

(65) Prior Publication Data
US 2015/0191475 A1    Jul. 9, 2015

(30) Foreign Application Priority Data

Jul. 4, 2012 (EP) .................................... 12174932

(51) Int. Cl.
*C07D 487/04* (2006.01)
*A61K 31/519* (2006.01)

(52) U.S. Cl.
CPC ............ *C07D 487/04* (2013.01); *A61K 31/519* (2013.01)

(58) Field of Classification Search
None
See application file for complete search history.

(56) References Cited

FOREIGN PATENT DOCUMENTS

| WO | 0034283 A1 | 6/2000 |
| WO | 0192262 A1 | 12/2001 |
| WO | 2010030224 A1 | 3/2010 |
| WO | 2011067571 A1 | 6/2011 |

OTHER PUBLICATIONS

International Search Report and Written Opinion, PCT/EP2013/064031, date of mailing Aug. 29, 2014, 9 pages.

*Primary Examiner* — Jeffrey H Murray
(74) *Attorney, Agent, or Firm* — Luedeka Neely Group, P.C.

(57) ABSTRACT

The present invention relates to amorphous adducts of ticagrelor with divalent metal salts useful in the treatment or prevention of arterial thrombotic complications in patients with coronary artery, cerebrovascular or peripheral vascular disease.

9 Claims, 9 Drawing Sheets

TICAGRELOR ADDUCTS WITH DIVALENT METAL SALTS

This application is a national phase entry of PCT International application number PCT/EP2013/064031, filed Jul. 3, 2013. This application also claims the benefit of the earlier filing date of: (1) EP 12174932.9, filed Jul. 4, 2012.

The present invention generally relates to adducts of ticagrelor with divalent metal salts. The present invention also generally relates to a pharmaceutical composition comprising the adduct(s), as well as to methods of using the adduct(s) in the treatment or prevention of arterial thrombotic complications in patients with coronary artery, cerebrovascular or peripheral vascular disease, and methods for obtaining such adduct(s).

BACKGROUND OF INVENTION

Ticagrelor (TCG; 3-[7-[[(1R,2S)-2-(3,4-difluorophenyl)cyclopropyl]amino]-5-(propylthio)-3H-1,2,3-triazolo[4,5-d]pyrimidin-3-yl]-5-(2-hydroxyethoxy)-(1S,2S,3R,5S)-1,2-cyclopentanediol) having the following structural formula

TCG shows pharmaceutical activity by functioning as a P2Y12 receptor antagonist and thus is indicated for the treatment or prevention of thrombotic events, for example stroke, heart attack, acute coronary syndrome or myocardial infection with ST elevation, other coronary artery diseases and arterial thrombosis as well as other disorders related to platelet aggregation (WO 2000/34283).

Ticagrelor (TCG) may exist in a number of different substantially crystalline forms (Polymorph I, Polymorph II, Polymorph III and Polymorph IV) as described in WO2001/092262.

In addition, WO2011/067571 discloses co-crystals of ticagrelor and a co-former molecule selected from glycolic acid, salicylic acid, decanoic acid, gentisic, acid, glutaric acid, vanillic acid, succinic acid, malonic acid and maltol.

International applications WO2000/034283 and WO2010/030224 describe a process of purification of ticagrelor by crystallization.

SUMMARY OF THE INVENTION

The present invention provides physically stable adducts of ticagrelor with divalent metal salts. Embodiments of these adducts include adducts with divalent alkaline earth metal salts, for example with $MgCl_2$, $MgBr_2$, $Mg(OAc)_2$, $CaCl_2$ and $Ca(OAc)_2$, as well as adducts with other divalent metal salts, for example with $FeCl_2$, $Fe(OAc)_2$.

The adducts of the present invention are highly useful as intermediates in industrially efficient purification and isolation of ticagrelor.

DESCRIPTION OF THE INVENTION AND OF PREFERRED EMBODIMENTS

Aspects, advantageous features and preferred embodiments of the present invention will be described in further detail below, noting however that such aspects, advantages features as well as embodiments and examples are presented for illustrative purposes only and shall not limit the invention in any way.

Ticagrelor (TCG) has low solubility in water. Due to a lack of stronger acidic or basic centers in the molecular structure, the opportunity for preparing salts with increased solubility is eliminated. Another option for improvement of solubility in water is preparation of different polymorphic forms. According to thermodynamic laws, however, the most stable form is usually the least soluble one, while less stable forms, which could be more soluble, may have a tendency for transformation into a more stable form, or are even chemically less stable. In addition, co-crystals, i.e. adducts, alternative to salts in cases wherein salts do not exist, in many cases exert labile intermolecular bonds, which might result in the partner molecule not being completely physiologically inert.

It has now been found that ticagrelor (3-[7-[[(1R,2S)-2-(3,4-difluorophenyl)cyclopropyl]amino]-5-(propylthio)-3H-1,2,3-triazolo[4,5-d]pyrimidin-3-yl]-5-(2-hydroxyethoxy)-(1 S,2S,3R,5S)-1,2-cyclopentanediol) can form adducts with metal cations. Since the molecule itself does not have acidic centers, which would allow the formation of a salt via metal-proton exchange, the existence of such adducts is highly surprising. The adducts can be easily isolated in physically and chemically stable solid forms.

The term "adduct" refers to a product of a direct addition of two or more distinct molecules, resulting in a single reaction/isolation product containing all atoms of all components.

The term "basic ticagrelor" used herein refers to ticagrelor not coupled with any other molecule or ion and is not to be associated with the term in the sense of alkalinity and Brønsted or Lewis basicity.

In one embodiment the present invention relates to an adduct comprising basic ticagrelor (TCG), a divalent metal cation and an anion. The adduct is represented by formula I wherein M represents a divalent metal cation ($M^{2+}$) and A represents a divalent anion, $Y^{2-}$, or two monovalent anions, $(X^-)_2$ or $(X^1)^-(X^2)^-$.

The divalent metal is preferably selected from an alkaline earth metal cation, copper(II), iron(II) and zinc. The term "alkaline earth metal" refers to metals of the second group of the periodic table that is to beryllium, magnesium, calcium, strontium, barium and radium. Preferred alkaline earth metal cations are physiologically acceptable ones such as $Mg^{2+}$, $Ca^{2+}$, or $Sr^{2+}$; particularly preferred metal cation is $Ca^{2+}$.

The anion is preferably selected from ions of mineral acids, low aliphatic acids, low aliphatic sulfonates, low alcoholates, and hydroxides. Anions of mineral acids are for example chlorides, bromides, iodides, nitrates, perchlorates, sulfates, hydrogensulfates, hydrogenphosphates, dihydrogenphosphates or a mixture thereof. Low aliphatic acid is selected from $C_1$-$C_5$-alkanoic acids, the preferable anion is acetate. Low aliphatic sulfonate is selected from unsubstituted or fluorinated $C_1$-$C_4$-alkanesulfonic acids, preferably the anion is mesylate or triflate. Low alcoholate is selected from $C_1$-$C_4$-alkoxides, the preferable alcoholate is ethoxide. Preferably, the anion originates from the metal salt, entering the process of formation of adducts of the present invention. Preferred metal salts used for the preparation of the adducts are selected from $MgCl_2$, $MgBr_2$, $Mg(OAc)_2$, $Mg(OH)_2$, $Mg(OEt)_2$, $CaCl_2$, $Ca(OAc)_2$, $SrCl_2$, $ZnCl_2$, $FeCl_2$ and $Fe(OAc)_2$, most preferred are $MgCl_2$, $MgBr_2$, $CaCl_2$, and $Fe(OAc)_2$. Salts incorporated in adducts can be in the form of separated ions, such as in the form of $M^{2+}$—$(X^1)^-$—, $M^{2+}$—$X^-$—$X^-$ or $M^{2+}$—$Y^{2-}$, or as a coupled moiety $MX^1X^2$, $MX_2$ or MY.

Schematic representation of adducts as TCG×MA is irrespective of MA being present as separated ions, a unique moiety or a mixture thereof.

Optionally, adducts TCG×MA are hydrated or solvated in a form of a stable structure $(TCG×MA)_mS_n$, wherein S is $H_2O$ or an organic solvent, while m and n are natural numbers, not regarding residual amounts of water or organic solvent due to insufficient drying or floating amounts due to hydroscopicity or solvophility.

Figure 1:
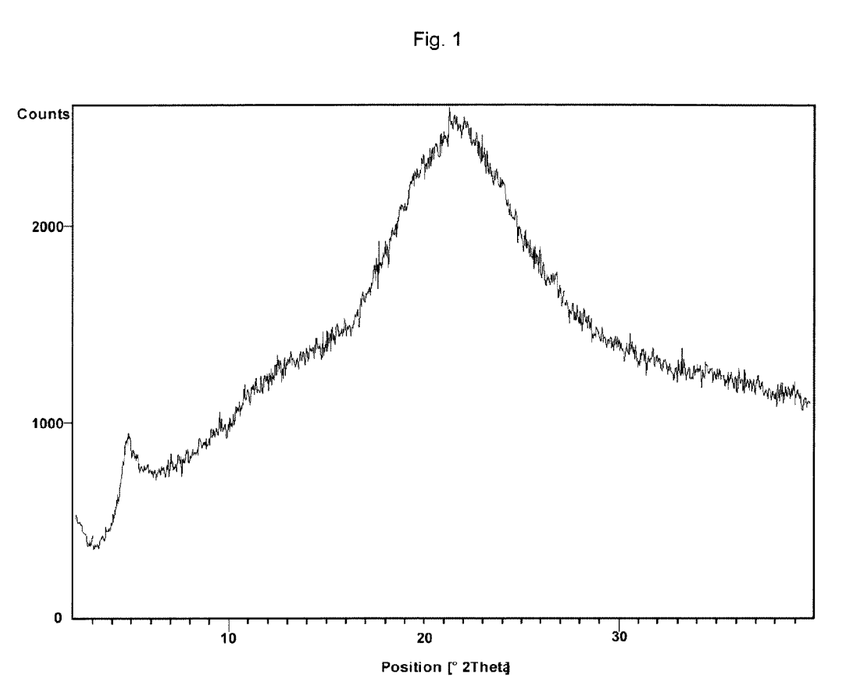
FIG. 1. illustrates the X-ray powder diffraction pattern of the TCG×$CaCl_2$ adduct.

The adducts of the present invention are amorphous according to X-Ray powder diffraction (FIG. 1). It was surprisingly found that the molar ratio between ticagrelor and the metal is fixed despite amorphicity. The molar amount of metal per mole of ticagrelor is 0.8 to 1.2 per 1, preferably 0.9 to 1.1 per 1, more preferably 0.96 to 1.04 per 1, most preferably 1:1. Therefore, the mixture is not a simple physical mixture of ticagrelor and a metal salt, but it has a tighter structure between both components. The product is chemically and physically stable and is not subdued to conversion to a crystalline form of ticagrelor. This is an essential difference in comparison to amorphous basic ticagrelor which quickly converts to the more stable crystalline forms. In this sense, a metal salt comprising the adduct can be regarded as a physical stabilizer of amorphous state of ticagrelor.

Adducts with divalent metal salts show better kinetic dissolution in aqueous testing media than the crystalline ticagrelor. Solubility can be important parameter in the preparation of pharmaceutical composition, dissolution of the dosage form and subsequently bioavailability, especially in the case of very low soluble compounds such as ticagrelor.

In a particularly preferred embodiment the present invention relates to an adduct of basic ticagrelor with $CaCl_2$. The adduct is represented by formula Ia This adduct may be employed in pharmaceutical compositions which may optionally include one or more components selected, for example, from the group consisting of excipients, carriers, and on of other active pharmaceutical ingredients, active chemical entities of different molecular structure.

In another particularly preferred embodiment the present invention relates to an adduct of basic ticagrelor with $MgCl_2$. The adduct is represented by formula Ib This adduct may be employed in pharmaceutical compositions which may optionally include one or more compo- nents selected, for example, from the group consisting of excipients, carriers, and on of other active pharmaceutical ingredients, active chemical entities of different molecular structure.

In another particularly preferred embodiment the present invention relates to an adduct of basic ticagrelor with $MgBr_2$. The adduct is represented by formula Ic This adduct may be employed in pharmaceutical compositions which may optionally include one or more components selected, for example, from the group consisting of excipients, carriers, and on of other active pharmaceutical ingredients, active chemical entities of different molecular structure.

In another particularly preferred embodiment the present invention relates to an adduct of basic ticagrelor with $Fe(OAc)_2$. The adduct is represented by formula Id This adduct may be employed in pharmaceutical compositions which may optionally include one or more components selected, for example, from the group consisting of excipients, carriers, and on of other active pharmaceutical ingredients, active chemical entities of different molecular structure.

In another embodiment the present invention relates to a method for preparation of an adduct comprising basic ticagrelor (TCG), a divalent metal cation (M) and an anion (A), wherein the divalent metal cation and the anion are defined as described above, the method comprising:
 (i) a reaction between the basic ticagrelor (TCG) and a metal salt (MA) in an aprotic solvent or a mixture of aprotic solvents,
 (ii) isolating the precipitate, and
 (iii) drying precipitate to the constant weight.

Preferably, the metal salt (MA), used for preparation of the adducts, is selected from the group comprising $MgCl_2$, $MgBr_2$, $Mg(OAc)_2$, $Mg(OH)_2$, $Mg(OEt)_2$, $CaCl_2$, $Ca(OAc)_2$, $SrCl_2$, $ZnCl_2$, $FeCl_2$ and $Fe(OAc)_2$, most preferably the metal salt is $MgCl_2$, $MgBr_2$, $CaCl_2$, or $Fe(OAc)_2$. The salt can be used either in its anhydrous or its hydrated form.

The aprotic solvent used in step (i) is selected in such way that it precipitates the adduct in technically applicable concentrations. Said solvent dissolves ticagrelor and precipitates the adduct after addition of the metal salt. Usually, at least 80% of total ticagrelor is consumed while producing a mixture, which is easily stirred and filtered. Suitable aprotic solvents are nitriles, preferably acetonitrile (MeCN), ketones, preferably acetone, and esters, preferably acetic acid esters. Solvents are preferably used in volumes of 2-50 ml per g of ticagrelor, most preferably in volumes of 5-20 ml per g of ticagrelor. Mixtures of said aprotic solvents can also be used. Particularly preferred aprotic solvents are acetonitrile, acetone, methyl acetate and ethyl acetate.

Optionally, said solvents are water wet, meaning that a water immiscible solvent can contain water up to saturation and a water miscible solvent can contain at most 5% of water. Such option is preferable in the case if the adduct forms a stable hydrate. Optionally a formation of hydrate may consume water from hydrated metal salt.

The reaction of step (i) is carried out in a suitable aprotic solvent and at temperatures, at which ticagrelor is soluble and the TCG×MA adduct is not. A suitable temperature range, in which the TCG×MA adduct precipitates from the aprotic solvent, is from 0-120° C., preferably from 20-80° C. The obtained mixture can be optionally cooled to −20° C. to room temperature before conducting step (ii).

In step (ii) of the reaction, the precipitate is isolated using any suitable method in the art, for example by either filtration or centrifugation. Optionally, the precipitate can be washed using the same aprotic solvent as in step (i), or using another, preferably aprotic solvent or a mixture of aprotic solvents, several times in order to eliminate related impurities and the optional residual inorganic material.

In step (iii) of the reaction the precipitate is dried to a constant weight. Any suitable method can be used, for example drying in vacuum at suitable temperatures, for example from 20-50° C., or drying during filtration on the frit in the air, in nitrogen or in any other gas flow.

In another embodiment, the method for preparation of adducts comprising basic ticagrelor (TCG), a divalent metal cation (M) and an anion (A) can serve as an efficient method for purification of ticagrelor as a standalone method or as a combined approach with prior art crystallisations of ticagrelor.

Purification is a challenging task in the preparation of pharmaceutically acceptable ticagrelor as the molecule contains five chiral centers, which raises the possibility of the presence of unwanted structurally closely related impurities.

The method of purification of the present invention is especially beneficial because the precipitation method in preparation of adducts can use different solvent systems than those for purification of ticagrelor itself and can subsequently remove impurities which cannot be eliminated efficiently by prior art methods. The better purification potential of the method of the present invention when compared to crystallization of ticagrelor according to known procedure is observed despite the amorphous nature of adducts. In order to test the purification ability three different experiments, in which the process of the invention is compared to the crystallization published in WO2010/030244, have been performed (Examples 7, 8 and 9). Preferred adducts used for the purpose of purification of ticagrelor are adducts of basic ticagrelor with iron(II) acetate, calcium bromide, and calcium chloride, most preferably calcium chloride.

The adducts of the present invention (TCG×MA) can be easily transformed back to basic ticagrelor by addition of mixture of water and an alcohol, preferably selected from $C_1$-$C_5$-alcohols, most preferably methanol or ethanol. Basic ticagrelor precipitates and is filtered off and separated from the solution of inorganic salt. Ticagrelor obtained in this manner is isolated as Polymorph II (nomenclature according to WO2001/092262). Retransformation of metal salt adducts to basic ticagrelor using said method does not form new impurities. The adduct can be transformed to basic ticagrelor during the technological process for preparation of the final dosage form, or is retained in an adduct form in order to reach better solubility and bioavailability effects.

In another embodiment, the various adducts of the present invention can be used in medicine. The adducts, optionally in a hydrated or a solvated form, may be used alone or in combination, or formulated with one or more excipients or other active pharmaceutical ingredients to provide formulations suitable for the treatment or prevention of arterial thrombotic complications in patients with coronary artery, cerebrovascular or peripheral vascular disease.

The administration form can be suitably chosen, e.g. a form suitable for oral, parenteral, rectal administration and/or administration by inhalation, and the dosage form may be solid, liquid, or powdery. Therefore, the pharmaceutical composition comprising the adduct of the present invention may suitably be in the form of tablets, pills, capsules, syrups, powders or granules for oral administration; or as sterile parenteral or subcutaneous solutions, suspensions for parenteral administration; or as suppositories for rectal administration.

Suitable excipients and/or carriers include, without being limited to, diluents, binders, disintegrants, lubricants, etc. For example, the adduct of the present invention, or particles comprising said adduct, are mixed with a carrier or binder substance, e.g. a mono-, di- or polysaccharide such as sugars and starch, a sugar alcohol or another polyol. For example, lactose, saccharose, sorbitol, mannitol, starch, cellulose derivatives, a binder such as polyvinylpyrrolidone, and a lubricant such as magnesium stearate, calcium stearate, polyethylene glycol, waxes, paraffin, and the like are mixed, and then compressed into tablets. The adduct of the present invention or particles containing the same may be coated by another substance. The powder mixture or particles containing the adduct of the present invention may also be dispensed into capsules.

In a further aspect of the present invention, a pharmaceutical composition comprising the ticagrelor compound prepared according to the present invention, that is by comprising the steps of preparing the adduct TCG×MA and its reconversion to ticagrelor as described above, can be prepared by mixing the compound with a pharmaceutically acceptable carrier and/or excipient, using parameters, conditions and components as described above.

In the following the present invention will be described in further detail by illustrative, non-limiting examples.

EXAMPLES

Example 1

Preparation of an Adduct of TCG with $CaCl_2$ (Ia)

To a solution of TCG (0.52 g) in dry MeCN (8 mL) at 60° C. $CaCl_2$ (0.11 g) was added in one portion, and the resulting reaction mixture was stirred at 60° C. for 16 h. White solid was filtered off, washed with MeCN, and dried to afford Ia as an off-white powder (0.58 g). DSC: no peaks; XRD analysis: no peaks (amorphous solid) (FIG. 1); IR (KBr): 3412, 2963, 2933, 2874, 1614, 1590, 1522, 1456, 1430, 1325, 1277, 1212, 1115, 1060, 772, 690, 668, 618, 581 cm-1.

The adduct TCG×$CaCl_2$ (Ia) was also prepared in EtOAc:
To a solution of TCG (0.52 g) in EtOAc (4 mL) at 60° C. $CaCl_2$ (0.12 g) was added in one portion, and the resulting reaction mixture was stirred at 60° C. for 2 h. White solid was filtered off, washed with EtOAc, and dried to afford Ia as a yellow powder (0.51 g). DSC: no peaks. The adduct TCG× $CaCl_2$ (Ia) was also prepared using $CaCl_2×2H_2O$ in MeCN:
To a solution of TCG (0.30 g) in MeCN (4 mL) at 60° C. $CaCl_2×2H_2O$ (93 mg) was added in one portion, and the resulting reaction mixture was stirred at 60° C. for 2 h. White solid was filtered off, washed with MeCN, and dried to afford Ia as a white powder (0.51 g). DSC: no peaks (amorphous solid); IR (KBr): 3426, 2964, 1616, 1523, 1456, 1327, 1277, 1212, 1116, 1059, 668 cm$^{-1}$.

The adduct TCG×$CaCl_2$ (Ia) was also prepared using $CaCl_2×2H_2O$ in EtOAc:
Mixture of TCG (5.22 g) and $CaCl_2×2H_2O$ (1.54 g) in EtOAc (25 mL) was stirred at 60° C. for 20 h. White solid was filtered off, washed with EtOAc, and dried to afford Ia as a white powder (6.7 g). IR (KBr): 3382, 2964, 2934, 2873, 1615, 1522, 1456, 1431, 1379, 1324, 1300, 1277, 1212, 1115, 1057, 772, 689, 668, 644, 618, 581 cm$^{-1}$.

Example 2

Preparation of an Adduct of TCG with $MgCl_2$ (Ib)

To a solution of TCG (0.30 g) in dry MeCN (4 mL) at 60° C. $MgCl_2$ (60 mg) was added in one portion, and the resulting reaction mixture was stirred at 60° C. for 16 h. Salts were filtered off under nitrogen to give Ib as a white powder (hygroscopic on air).

Example 3

Preparation of an Adduct of TCG with $MgBr_2$ (Ic)

To a solution of TCG (0.20 g) in dry MeCN (5 mL) at 50° C. $MgBr_2$ (74 mg) was added in one portion, and the resulting reaction mixture was stirred at 50° C. for 15 min. Salts were filtered off under nitrogen to give Ic as a white powder (hygroscopic on air).

Example 4

Preparation of an Adduct of TCG with $Fe(OAc)_2$ (Id)

To a solution of TCG (0.20 g) in dry MeCN (4 mL) at 50° C. $Fe(OAc)_2$ (70 mg) was added in one portion, and the resulting reaction mixture was stirred at 50° C. for 16 h. Salts were filtered off, washed with MeCN, and dried to afford Id as a yellow powder (0.14 g). DSC: no peaks; XRD analysis: no peaks (amorphous solid); IR (KBr): 3426, 2962, 2932, 2873, 1608, 1522, 1446, 1324, 1276, 1211, 1115, 1061, 666 cm$^{-1}$.

Example 5

Preparation of TCG from the Adduct of TCG with $CaCl_2$ (Ia)

Mixture of Ia (0.20 g), $H_2O$ (3 mL) and MeOH (1 mL) was stirred at 25° C. for 16 h. White powder was filtered off, washed with water and dried to afford 0.12 g of TCG. DSC: Onset 132.2° C., Peak 135.8° C.; $^{19}F$ NMR (CD$_3$OD, 470.5 MHz) δ −141.9--142.1 (m, 1F), −145.6--145.9 (m, 1F); IR (KBr): 3392, 3293, 2963, 2931, 1625, 1589, 1521, 1452, 1427, 1329, 1291, 1276, 1208, 1196, 1114, 1072, 1050, 994, 891, 771, 668, 618, 579 cm$^{-1}$; MS (ESI) m/z: 523 [MH]+.

Example 6

Physical Stability of the Adduct of TCG with $CaCl_2$ (Ia) Compared to Amorphous TCG a) Preparation of Adduct of TCG with $CaCl_2$ (Ia) in EtOAc Mixture of TCG (3.0 g) and $CaCl_2×2H_2O$ (0.89 g) in EtOAc (40 mL) was stirred at 40° C. for 18 h. White solid was filtered off, washed with EtOAc (2×20 mL), and dried to afford Ia as a white powder (3.9 g).

Figure 2:
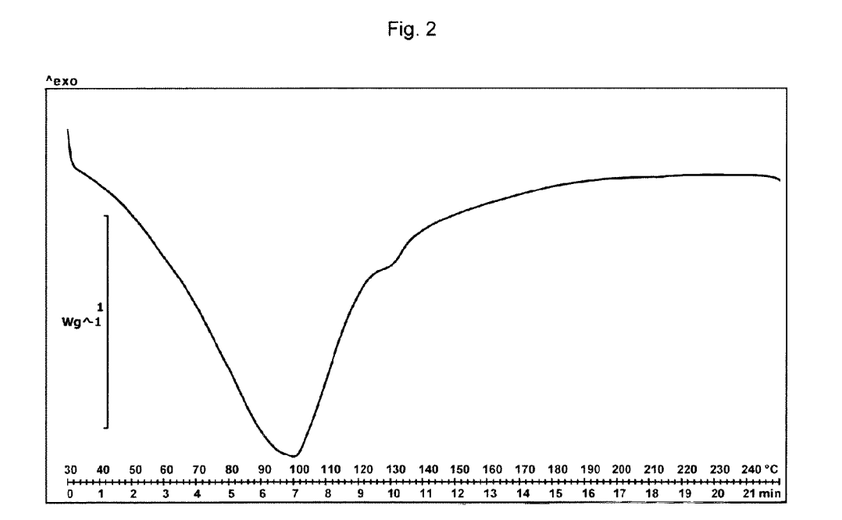
FIG. 2. illustrates the DSC thermogram of the TCG×$CaCl_2$ adduct prepared in Example 6 a) after 21 days.
Figure 3:
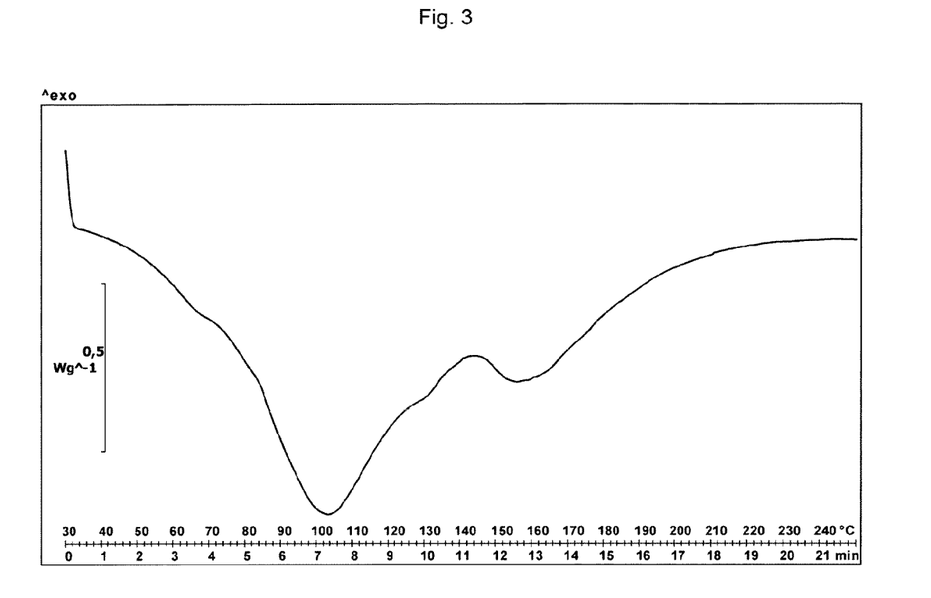
FIG. 3. illustrates the DSC thermogram of the TCG×$CaCl_2$ adduct prepared in Example 6 a) after 31 days.

The so obtained Ia was left at room temperature in a closed vial to test physical stability. DSC analysis was performed after 21 days (FIG. 2) and after 31 days (FIG. 3).

b) Preparation of Adduct of TCG with $CaCl_2$ (Ia) in MeOAc

Mixture of TCG (5.22 g) and $CaCl_2 \times 2H_2O$ (1.40 g) in MeOAc (60 mL) was stirred at 25° C. for 20 h. White solid was filtered off, washed with MeOAc (2×30 mL), and dried to afford Ia as a white powder (6.3 g).

c) Purification of TCG Using Adduct Ia

Figure 10:
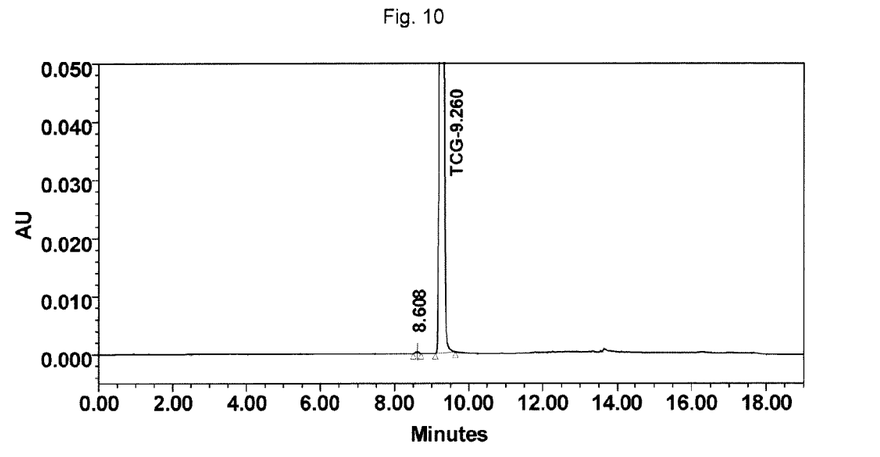
FIG. 10. illustrates the UPLC diagram of the TCG×$CaCl_2$ adduct according to Example 7 c).

A mixture of the test sample prepared under a) (0.52 g) and $CaCl_2 \times 2H_2O$ (0.13 g) in EtOAc (5 mL) was stirred at 50° C. for 16 h. White solid was filtered off, washed with EtOAc (2×5 mL), and dried to afford Ia as a white powder (0.57 g). UPLC analysis is shown in FIG. 10.

Figure 11:
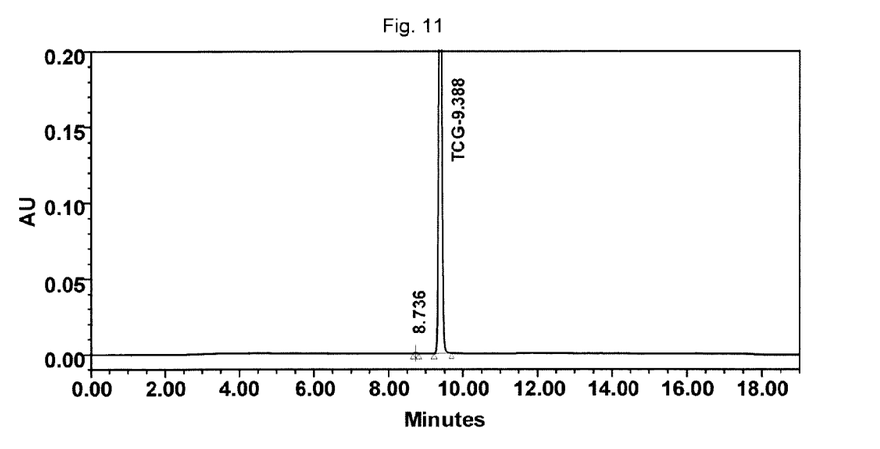
FIG. 11. illustrates the UPLC diagram of the purified TCG according to Example 7 c).

In the next step, the obtained adduct Ia was transformed back to TCG. Mixture of Ia (0.57 g), $H_2O$ (10 mL) and MeOH (10 mL) was stirred at 25° C. for 2 days. Water was then added (10 mL), white powder was filtered off, washed with water (2×5 mL) and dried to afford 0.48 g (92% yield) of TCG. UPLC analysis of the so obtained TCG is shown in FIG. 11.

TABLE I

Comparison of purification processes of Example 7

| | | % Area | | | |
|---|---|---|---|---|---|
| Compound name | Retention time (min) | Example a) | Example b) | Example c) - adduct | Example c) - TCG |
| unknown | 8.728, 8.614, 8.608 | 0.07 | 0.06 | 0.08 | 0.07 |
| TCG | 9.380, 9.272, 9.260 | 93.37 | 99.79 | 99.92 | 99.94 |
| unknown | 13.398 | 0.06 | / | / | / |
| CLIN | 13.564, 13.558, 13,660 | 6.47 | 0.15 | / | / |
| unknown | 14.134 | 0.03 | / | / | / |

Figure 4:
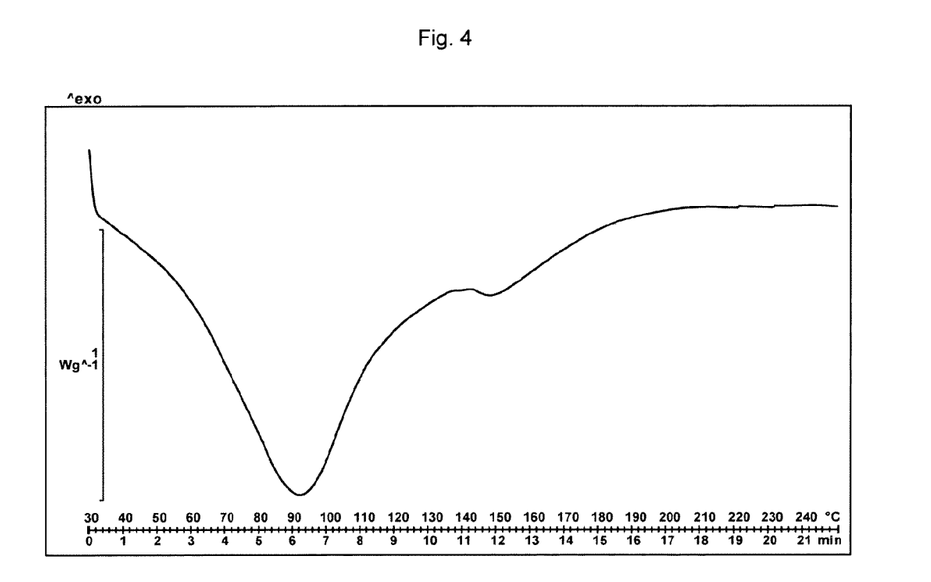
FIG. 4. illustrates the DSC thermogram of the TCG×$CaCl_2$ adduct prepared in Example 6 b).
Figure 5:
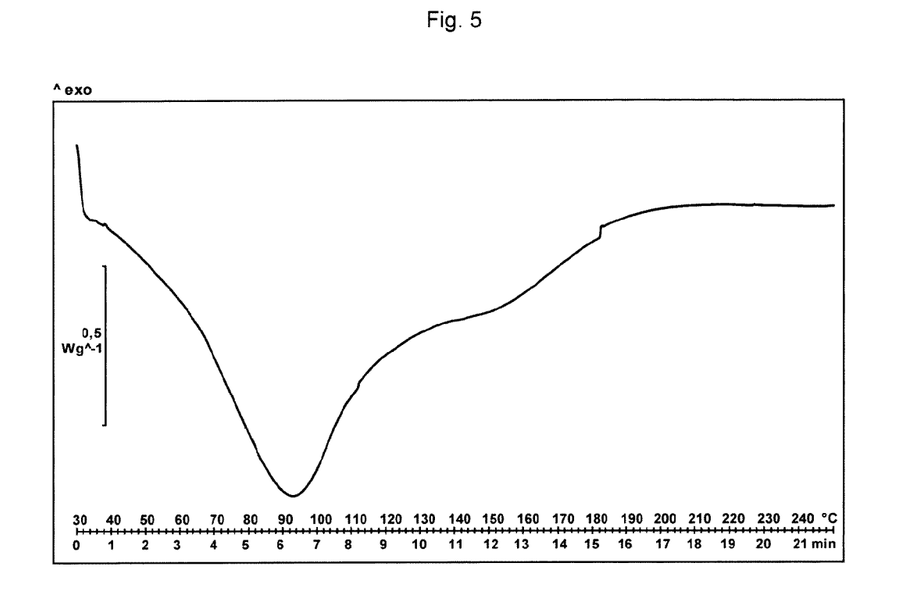
FIG. 5. illustrates the DSC thermogram of the TCG×$CaCl_2$ adduct prepared in Example 6 b) after 4 days.

DSC analysis of a sample was performed immediately (FIG. 4). Another sample of the so obtained Ia was left at room temperature to test physical stability. DSC analysis after 4 days is presented in FIG. 5.

c) Preparation of Amorphous TCG

Figure 6:
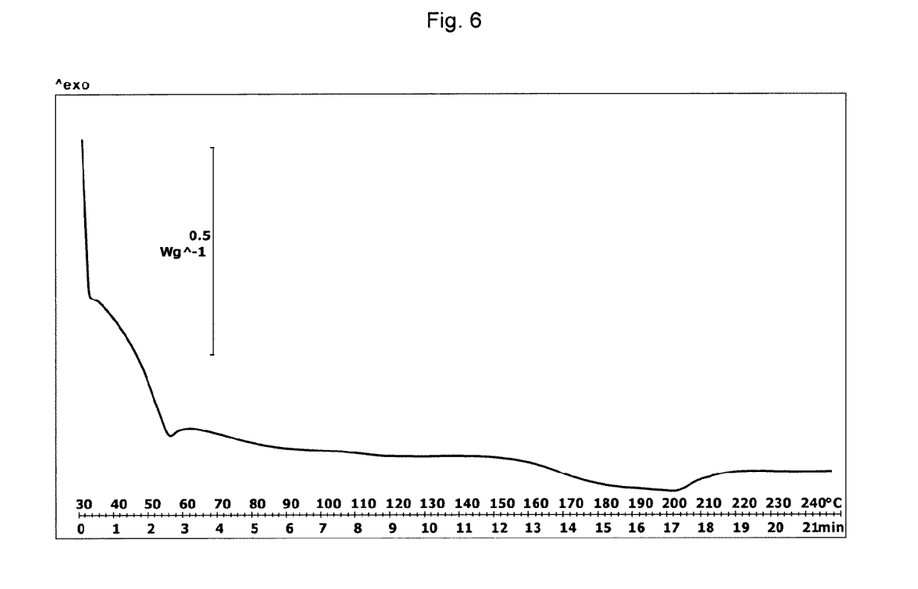
FIG. 6. illustrates the DSC thermogram of the amorphous TCG prepared in Example 6 c).
Figure 7:
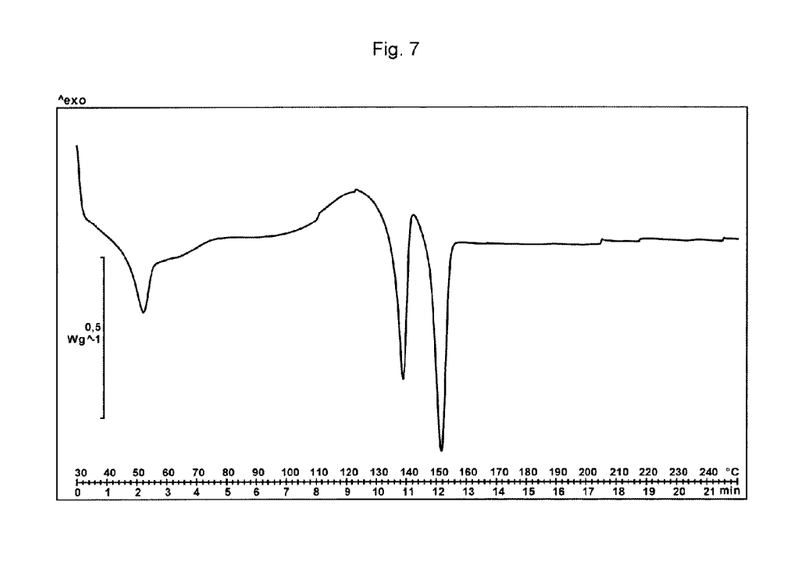
FIG. 7. illustrates the DSC thermogram of the amorphous TCG prepared in Example 6 c) after 1 day.

TCG (0.52 g) was dissolved in 55 mL of aqueous ethanol (50 vol %) with the aid of ultrasonic irradiation. To the solution 33 mL water was poured at once and the obtained turbid mixture was frozen immediately in liquid nitrogen. The material was then lyophilized for 72 h at ~0.8 mbar. DSC analysis of a sample was performed immediately (FIG. 6). Another sample of the so obtained amorphous TCG was left at room temperature to test physical stability. DSC analysis after 1 day is presented in FIG. 7.

Example 7

Purification of TCG Using Adduct Ia a) Preparation of Test Sample

Figure 8:
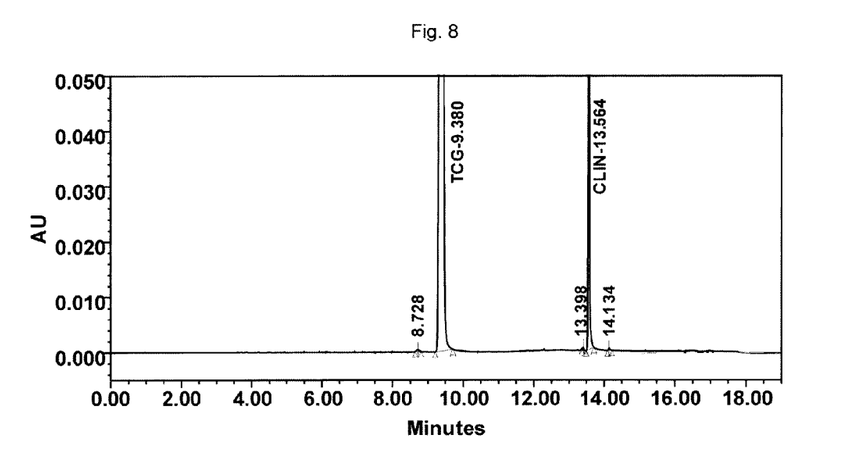
FIG. 8. illustrates the UPLC diagram of the test sample prepared in Example 7 a).

For demonstration of purification power of adduct Ia, a mixture of pure TCG and acetonide protected TCG (CLIN-2-(((3aR,4S,6R,6aS)-6-(7-(((1R,2S)-2-(3,4-difluorophenyl)cyclopropyl)-amino)-5-(propylthio)-3H-[1,2,3]triazolo[4,5-d]pyrimidin-3-yl)-2,2-dimethyltetrahydro-3aH-cyclopenta[d][1,3]dioxol-4-yl)oxy)ethanol) at 13.56 min was prepared. UPLC analysis of the mixture is shown in FIG. 8.

b) Comparative Example

Figure 9:
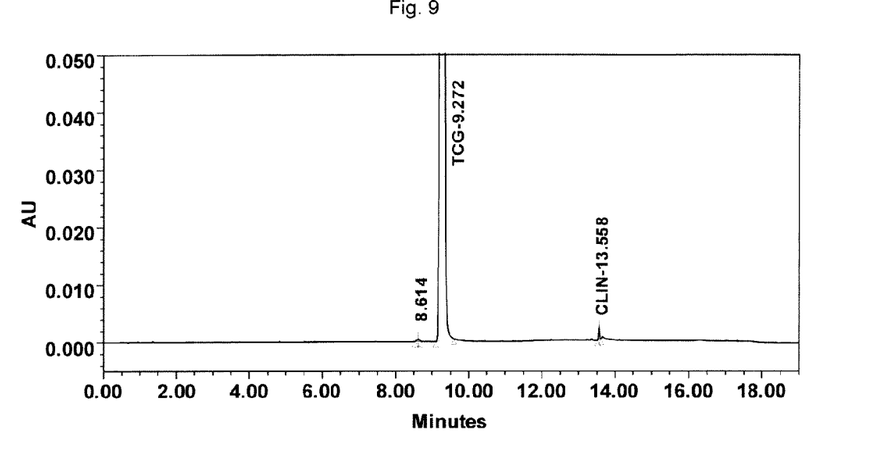
FIG. 9. illustrates the UPLC diagram of the purified TCG according to comparative Example 7 b)

The test sample prepared under a) was first purified according to the crystallization procedure described in WO 2010/030244. Test sample (0.50 g) was dissolved in 3.4 mL EtOAc at 57° C. Solution was then cooled to 50° C. and 3.2 mL isooctane was added at this temperature in 1.72 h. The mixture was then stirred at 50° C. for 16 h, then it was cooled to 0° C., and white powder was filtered off, washed with to 0° C. cooled mixture EtOAc/isooctane=1:1 (5 mL) and dried to afford white powder (0.41 g, 82% yield). UPLC analysis is shown in FIG. 9.

Example 8

Purification of TCG Using Adduct Ia a) Test Sample

Figure 12:
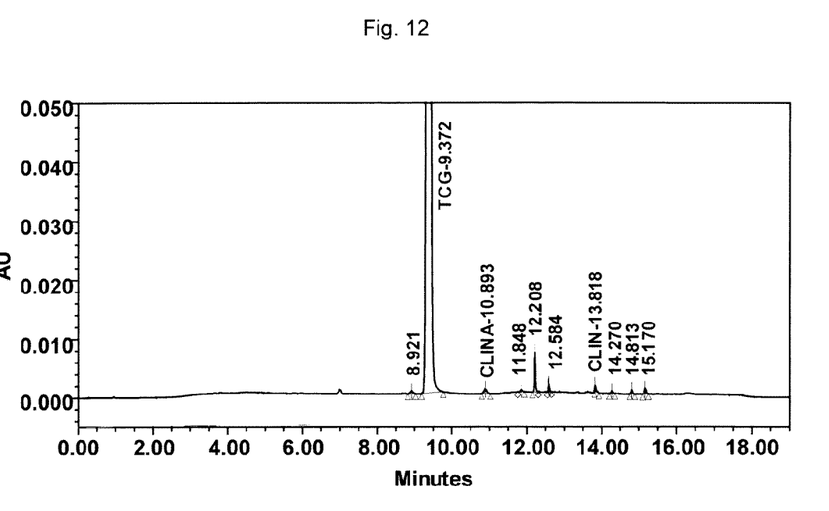
FIG. 12. illustrates the UPLC diagram of the test sample prepared in Example 8 a).

For demonstration of purification power of adduct Ia a real sample of TCG with several impurities was used. UPLC analysis is shown in FIG. 12.

b) Comparative Example

Figure 13:
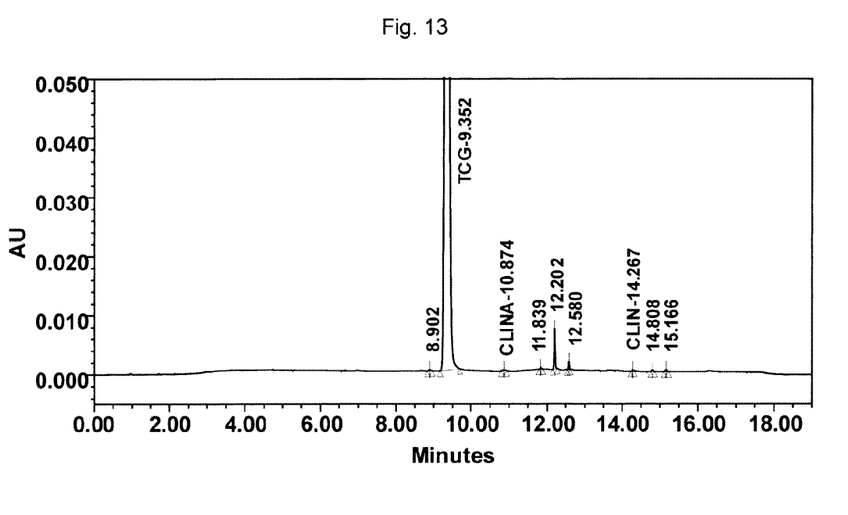
FIG. 13. illustrates the UPLC diagram of the purified TCG according to comparative Example 8 b).

The test sample under a) was first purified according to the crystallization procedure described in WO 2010/030244. Test sample (0.50 g) was dissolved in 3.4 mL EtOAc at 57° C. Solution was then cooled to 50° C. and 3.2 mL isooctane was added at this temperature in 1.72 h. The mixture was then stirred at 50° C. for 1 h, then it was cooled to 0° C. in 2.35 h, and stirred at 0° C. for 2.33 h. White powder was then filtered off, washed with to 0° C. cooled mixture EtOAc/isooctane=1:1 (5 mL) and dried to afford an off-white powder (0.40 g, 80% yield). UPLC analysis is shown in FIG. 13.

c) Purification of TCG Using Adduct Ia

Figure 14:
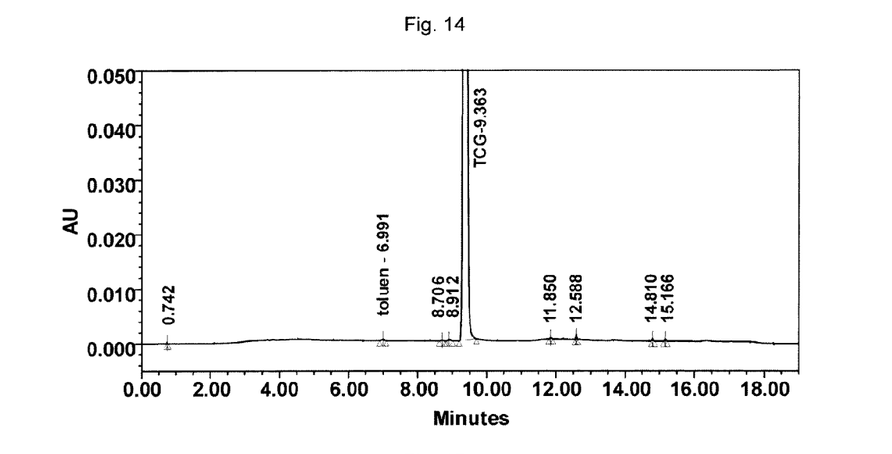
FIG. 14. illustrates the UPLC diagram of the TCG×$CaCl_2$ adduct according to Example 8 c).

A mixture of the test sample under a) (0.30 g) and $CaCl_2 \times 2H_2O$ (76 mg) in acetone (5 mL) was stirred at 25° C. for 16 h. White solid was filtered off, washed with acetone (2×5 mL), and dried to afford Ia as a white powder (0.38 g). UPLC analysis is shown in FIG. 14.

Figure 15:
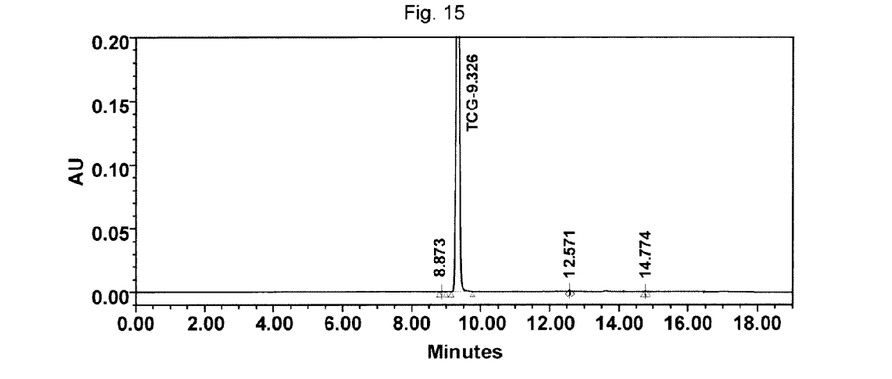
FIG. 15. illustrates the UPLC diagram of the purified TCG according to Example 8 c).

In the next step, the obtained adduct Ia was transformed back to TCG. Mixture of Ia (0.38 g), $H_2O$ (5 mL) and MeOH (5 mL) was stirred at 25° C. for 2 h. Water was then added (5 mL), white powder was filtered off, washed with water (5 mL) and dried to afford 0.28 g (93% yield) of TCG. UPLC analysis is shown in FIG. 15.

TABLE II

Comparison of purification processes of Example 8

| | | % Area | | | |
|---|---|---|---|---|---|
| Compound name | Retention time (min) | Example a) | Example b) | Example c) - adduct | Example c) - TCG |
| unknown | 0.742 | / | / | 0.01 | / |
| unknown | 6.991 | / | / | 0.04 | / |
| unknown | 8.706 | / | / | 0.02 | / |
| unknown | 8.921, 8.902, 8.912, 8.873 | 0.08 | 0.03 | 0.04 | 0.05 |
| TCG | 9.372, 9.352, 9.363 | 98.89 | 99.32 | 99.73 | 99.85 |
| CLINA | 10.893, 10.874 | 0.13 | 0.03 | / | / |
| unknown | 11.848, 11.839, 11.850 | 0.04 | 0.03 | 0.03 | / |
| unknown | 12.208, 12.202 | 0.48 | 0.43 | / | ? |
| unknown | 12.584, 12.580, 12.588, 12.571 | 0.08 | 0.07 | 0.04 | 0.05 |
| CLIN | 13.818 | 0.10 | / | / | / |
| unknown | 14.270, 14.267* | 0.03 | 0.02 | / | / |
| unknown | 14.813, 14.808, 14.810, 14.774 | 0.07 | 0.03 | 0.05 | 0.05 |
| unknown | 15.170, 15.166, 15.166 | 0.09 | 0.03 | 0.03 | / |

*In FIG. 13 the machine automatically marked this impurity as CLIN, however compared to other peaks it should be the impurity that follows CLIN.

Example 9

Purification of TCG Using Adduct Ia a) Test Sample

Figure 16:
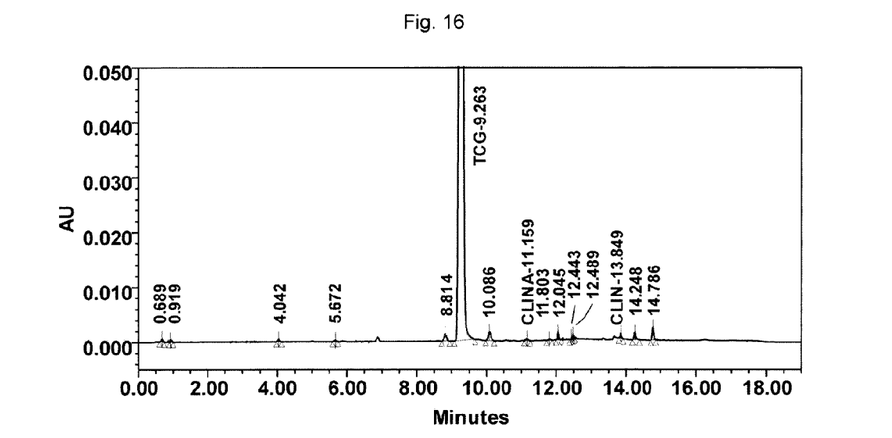
FIG. 16. illustrates the UPLC diagram of the test sample prepared in Example 9 a).

For demonstration of purification power of adduct Ia a real sample of TCG with several impurities was used. UPLC analysis is shown in FIG. 16.

b) Comparative Example

Figure 17:
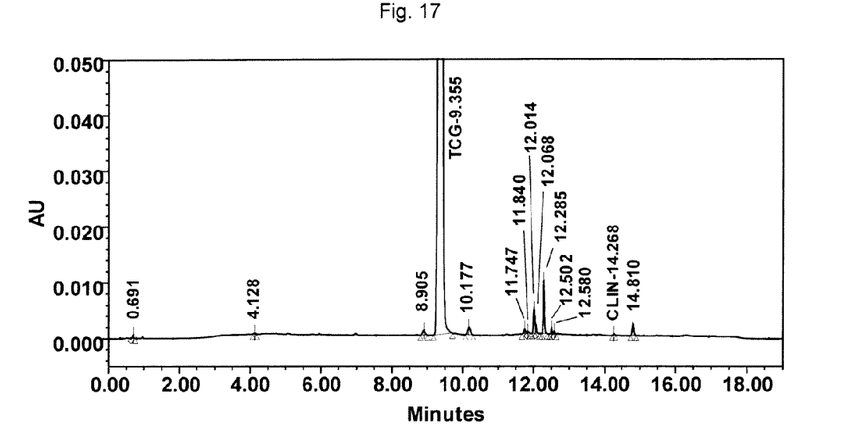
FIG. 17. illustrates the UPLC diagram of the purified TCG according to comparative Example 9 b).

The test sample under a) was first purified according to the crystallization procedure described in WO 2010/030244. Test sample (0.42 g) was dissolved in 2.8 mL EtOAc at 57° C. Solution was then cooled to 50° C. and 2.7 mL isooctane was added at this temperature in 1.72 h. The mixture was then stirred at 50° C. for 1 h, then it was cooled to 0° C. in 2.35 h, and stirred at 0° C. for 2.33 h. White powder was then filtered off, washed with to 0° C. cooled mixture EtOAc/isooctane=1:1 (5 mL) and dried to afford a beige powder (0.33 g, 79% yield). UPLC analysis is shown in FIG. 17.

c) Purification of TCG Using Adduct Ia

Figure 18:
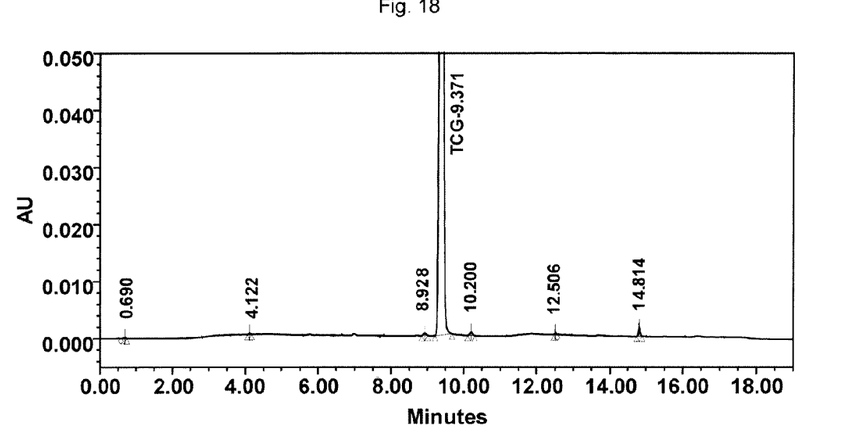
FIG. 18. illustrates the UPLC diagram of the TCG×$CaCl_2$ adduct according to Example 9 c).

The mixture of the test sample under a) (0.30 g) and $CaCl_2 \times 2H_2O$ (76 mg) in acetone (5 mL) was stirred at 25° C. for 16 h. White solid was filtered off, washed with acetone (2×5 mL), and dried to afford Ia as an off-white powder (0.36 g). UPLC analysis is shown in FIG. 18.

Figure 19:
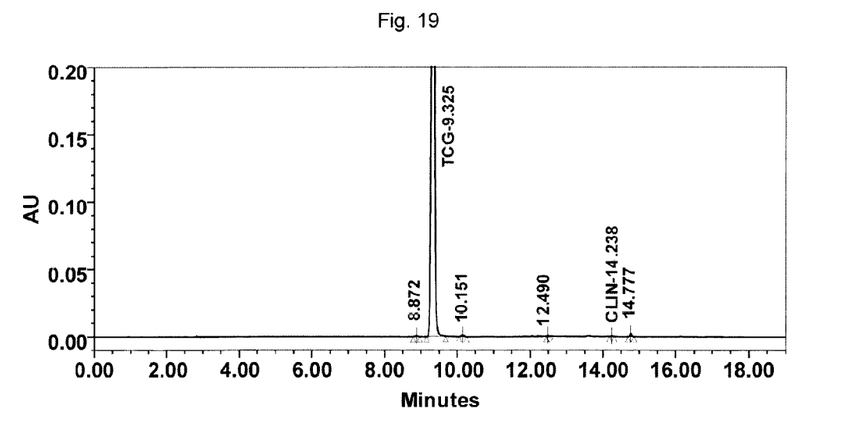
FIG. 19. illustrates the UPLC diagram of the purified TCG according to Example 9 c).

In the next step, the obtained adduct Ia was transformed back to TCG. Mixture of Ia (0.36 g), $H_2O$ (5 mL) and MeOH (5 mL) was stirred at 25° C. for 2 h. Water was then added (5 mL), white powder was filtered off, washed with water (5 mL) and dried to afford 0.28 g (93% yield) of TCG. UPLC analysis is shown in FIG. 19.

TABLE III

Comparison of purification processes of Example 9

| | | % Area | | | |
|---|---|---|---|---|---|
| Compound name | Retention time (min) | Example a) | Example b) | Example c) - adduct | Example c) - TCG |
| uknown | 0.689, 0.691, 0.690 | 0.05 | 0.05 | 0.04 | / |
| uknown | 0.919 | 0.04 | / | / | / |
| uknown | 4.042, 4.128, 4.122 | 0.05 | 0.02 | 0.04 | / |
| uknown | 5.672 | 0.03 | / | / | / |
| uknown | 8.814, 8.905, 8.928, 8.872 | 0.23 | 0.13 | 0.12 | 0.14 |
| TCG | 9.263, 9.355, 9.371 | 98.56 | 98.08 | 99.36 | 99.34 |
| uknown | 10.086, 10.177, 10.200, 10.151 | 0.29 | 0.22 | 0.16 | 0.20 |
| CLINA | 11.159 | 0.06 | / | / | / |
| unknown | 11.747 | / | 0.08 | / | / |
| unknown | 11.803, 11.840 | 0.03 | 0.03 | / | / |
| unknown | 12.045, 12.014 | 0.11 | 0.32 | / | / |
| unknown | 12.068 | / | 0.12 | / | / |
| unknown | 12.443, 12.285 | 0.03 | 0.64 | / | / |
| unknown | 12.489, 12.502, 12.506, 12,490 | 0.05 | 0.05 | 0.04 | 0.05 |
| unknown | 12.580 | / | 0.03 | / | / |
| CLIN | 13.849 | 0.08 | / | / | / |
| unknown | 14.248, 14.268*, 14,238* | 0.15 | 0.03 | / | 0.04 |

Example 10

Determination of Solubility

Figure 20:
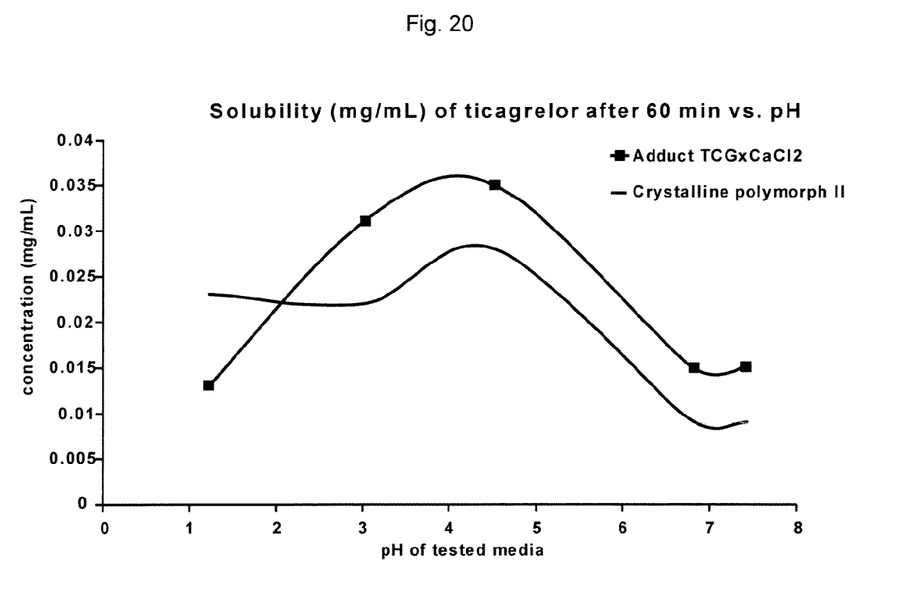
FIG. 20. illustrates pH-dependent solubility of TCG×$CaCl_2$ adduct in comparison to crystalline TCG (Polymorph II) after 1 h.

Solubility of adduct Ia and crystalline ticagrelor (Polymorph II) in aqueous medium has been determined at T=37° C., 1 h, stirring at 400 rpm. The results are shown in FIG. 20.

Methods of Analysis

X-Ray Powder Diffraction Method:

Conditions for obtaining powder X-ray diffraction (XRD) patterns: The powder X-ray diffraction patterns were obtained by methods known in the art using Philips X'Pert PRO diffractometer with X'Celerator detector using CuKα radiation (tube operating at 45 kV and 40 mA) in the Bragg-Brentano (reflection) geometry. Data were recorded from 2 to 40°2θ in steps of 0.033°2θ and the measurement time of 50 seconds per step. Variable divergence and antiscatter slits were used to maintain 12 mm of sample length irradiated.

Differential Scanning Calorimetry:

Conditions for obtaining DSC thermograms: Thermograms were obtained with Mettler Toledo DSC822e differential scanning calorimeter. The sample (1-10 mg) was placed in an unsealed aluminium pan with a hole and heated at 10° C./min in the temperature range from 30° C. to 250° C.

Ultra Performance Liquid Chromatography (UPLC):

Chromatographic purity of all intermediates and ticagrelor was determined by UPLC analytical method. An acquity HSS T3 100×2.1 mm, 1.8 um column with flow rate of 0.4 ml/min at 25° C. was used. A gradient elution from 7 to 80% of mobile phase B was applied. Mobile phase A was constituted from 70% of 2 mM ammonium acetate buffer (pH 4.8) and 30% of acetonitrile. Mobile phase B was 100% acetonitrile. Absorbance chromatograms were recorded at 265 nm.

The invention claimed is:

1. An adduct of a compound of formula I with a divalent metal salt

I

2. The adduct according to claim 1, wherein the divalent metal salt is alkaline earth metal salt, $ZnCl_2$, $FeCl_2$ or $Fe(OAc)_2$.

3. The adduct according to claim 2, wherein the alkaline earth metal salt is selected from the group consisting of $MgCl_2$, $MgBr_2$, $Mg(OAc)_2$, $Mg(OH)_2$, $Mg(OEt)_2$, $CaCl_2$, $Ca(OAc)_2$, and $SrCl_2$.

4. The adduct according to claim 1 represented by formula Ia

Ia

5. The adduct according to claim 1 represented by formula Ib

Ib

6. A pharmaceutical composition comprising the adduct according to claim 1 and a pharmaceutically acceptable carrier or diluent.

7. A process for preparing the adduct of claim 1, comprising:
   a. providing the compound of formula I, and
   b. reacting the compound of formula I with a divalent metal salt or its hydrate in an aprotic solvent to yield the adduct of claim 1.

8. A process for purification of the compound of formula I, comprising:
   a. providing the adduct of claim 1,
   b. contacting the provided adduct with a mixture of water and alcohol,
   c. isolating the precipitated pure compound of formula I.

9. A method for the treatment or prevention of arterial thrombotic complications in patients with coronary artery, cerebrovascular or peripheral vascular disease, the method comprising administering to a patient a dosage form comprising an adduct according to claim 1.

* * * * *